United States Patent [19]

Knoll et al.

[11] 4,027,024

[45] * May 31, 1977

[54] PHARMACEUTICAL COMPOSITION HAVING SYNERGISTIC ANALGESIC ACTIVITY

[75] Inventors: József Knoll; Zsuzsanna Fürst; Zoltán Mészaros; Péter Szentmiklósi; Ágoston Dávid; István Hermecz; Attila Mándi, all of Budapest; Rezsö Bognár; Sándor Makleit, both of Debrecen; Gyula Valovics, Tiszavasvari; László Szávik, Tiszavasvari; Sándor Nagy, Tiszavasvari, all of Hungary

[73] Assignee: Chinoin Gyogyszer-es Vegyeszeti Termekek Gyara RT, Budapest, Hungary

[ * ] Notice: The portion of the term of this patent subsequent to May 4, 1993, has been disclaimed.

[22] Filed: Jan. 15, 1976

[21] Appl. No.: 649,237

Related U.S. Application Data

[63] Continuation-in-part of Ser. No. 415,749, Nov. 14, 1973, Pat. No. 3,954,986.

[30] Foreign Application Priority Data

Dec. 19, 1972 Hungary .............................. CI 1322

[52] U.S. Cl. ................................ 424/251; 424/260
[51] Int. Cl.² .............. A61K 31/485; A61K 31/505
[58] Field of Search ........................... 424/251, 260

[56] References Cited

UNITED STATES PATENTS 3,954,986   5/1976   Knoll et al. .............. 424/251

FOREIGN PATENTS OR APPLICATIONS 1,209,946   10/1970   United Kingdom

OTHER PUBLICATIONS

Bognar et al., Acta Chem. Acad. Sci., Hung., 58, pp. 203–205, (1968).

Primary Examiner—Stanley J. Friedman
Attorney, Agent, or Firm—Karl F. Ross; Herbert Dubno

[57] ABSTRACT

Pharmaceutical compositions of synergistic analgesic activity are provided which comprise an azido compound of the following formula:

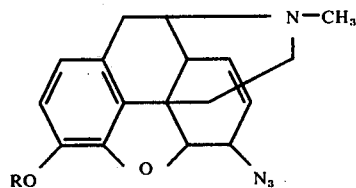

or a salt thereof wherein R is hydrogen, methyl, ethyl, acetyl or morpholino-methyl and a compound of the formula:

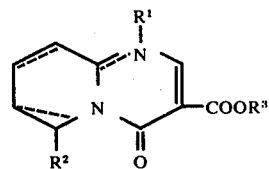

wherein $R^1$, $R^2$, $R^3$ are hydrogen or lower alkyl and the dotted lines represent hydrogenated bonds or olefinic bonds and pharmaceutically acceptable salts and quaternary salts thereof, in admixture with suitable inert solid or liquid carriers or dilutents.

8 Claims, No Drawings

PHARMACEUTICAL COMPOSITION HAVING SYNERGISTIC ANALGESIC ACTIVITY

CROSS-REFERENCE TO RELATED APPLICATION

This application is a continuation in part of Ser. No. 415,749 filed 14 Nov. 1973, now U.S. Pat. No. 3,954,986.

FIELD OF THE INVENTION

The present invention relates to pharmaceutical compositions having synergistic analgesic activity and a process for the preparation thereof.

BACKGROUND OF THE INVENTION

For the relief of postoperational pain and in the case of cancer patients in an advanced stage of the disease morphine and its derivatives are the most frequently used efficient analgesics. It is a well known fact, however, that in patients treated with morphine, harmful side-effects, e.g., respiratory depression, tolerance, and dependence, develop in a relatively short time. The patient gets used to morphine and rapidly rising doses are required to obtain an equianalgesic effect; tolerance or dependence develops and the patient is in permanent need of the euphorizing effect of morphine. Another disadvantage of morphine is the fact that it is practically ineffective on oral application.

All the analgesics suited for the treatment of unbearable pain (e.g. cancer, postoperative conditions, infarction, lithiases, etc.) are liable to induce the development of tolerance on chronic administration and their withdrawal produces severe — often fatal — somatic and psychic symptoms (physical and psychic dependence). It is generally accepted (Martin, 1967, Pharm. Rev. 19, 463) that the appearance of tolerance and dependence necessarily accompany the action of the morphine type drugs on the analgesic receptors. An analgesic equipotent to morphine, but devoid of its narcotic side-effects, has for long been needed in clinical practice.

OBJECT OF THE INVENTION

It is therefore the object of this invention to provide an analgesic which is both equipotent to morphine and totally devoid of its narcotic side-effects.

SUMMARY OF THE INVENTION

According to the present invention there is provided a pharmaceutical composition of synergistic analgesic activity comprising at least one azidocompound of the formula

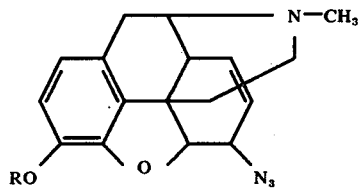

or a salt thereof (wherein R is hydrogen, methyl, ethyl, acetyl or morpholino-methyl) and at least one compound selected from the group consisting of compounds of the formula

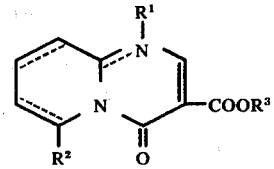

(wherein $R^1$, $R^2$ and $R^3$ are hydrogen or lower alkyl and the dotted lines represent olefinic or hydrogenated bonds) and pharmaceutically acceptable salts and quaternary salts thereof in admixture with suitable inert solid or liquid carriers or diluents.

The present invention is based on the recognition that some homopyrimidazole derivatives potentiate the analgesic action of the azido-compounds to a significant extent while having an advantageous influence on their other properties. A further advantage resides in the fact that the combinations according to the present invention are devoid of narcotic side effects.

The compositions according to the present invention may contain preferably azidoacetyl-morphine or azido-morpholino-methyl-morphine as the azido component. These compounds may be used in the form of the free base or as pharmaceutically acceptable acid addition salts. It is preferred to use the bitartarate salts which possess advantageous solubility properties.

In the homopyrimidazole compounds the alkyl groups may be straight or branched chained and contain 1-6, preferably 1-4 carbon atoms (e.g. methyl, ethyl, n-propyl, isobutyl, etc.). The salts and quaternary salts of the homopyrimidazole compounds include any pharmaceutically acceptable anion (e.g. inorganic anions, such as nitrate, chloride, bromide or sulphate anion; and organic anions e.g. methylsulphate, ethylsulphate etc.). A particularly preferred representative of the homopyrimidazole compounds is the 1,6-dimethyl-3-carbethoxy-4-oxo-6,7,8,9-tetrahydro-homopyrimidazolium-methosulphate.

Preferred compositions according to the present invention contain azidomorphine, azidocodeine, or the bitartarate thereof as the azido compound and 1,6-dimethyl-3-ethoxycarbonyl-4-oxo-6,7,8,9-tetrahydro-homopyrimidazolium-methosulphate as the homopyrimidazole compound.

The active ingredients of the synergistic combinations of the present invention are known. The azido compounds and the preparation thereof are described by R. Bognár and S. Makleit: Acta Chim. Acad. Sci. Hung. 58, 203 (1968). The homopyrimidazole derivatives and salts and quaternary salts thereof and also the preparation of these compounds is described in our Austrian Pat. Nos. 294,107 and 296,996.

The relative amount of the active ingredients in the combination according to the present invention may vary between wide ranges. It may be stated that the composition may contain about 20–1000 parts by weight of a homopyrimidazole compound of the formula (II) per 1 part by weight of an azido-compound. This broad range of proportions is effective for all of the compounds generically defined in the foregoing and claimed herein.

The pharmaceutical compositions may be finished in dosage forms suitable for oral or parenteral administration. The oral forms may be tablets, capsules, pills, coated pills etc. while the parenteral dosage forms may be injectable preparations, powders ampoules etc.

The pharmaceutical combinations of the present invention comprising azidocodeine or a salt thereof as the axido compound are suitable for oral administration (tablets, capsules) too. This oral dosage form is particularly advantageous, since in clinical practice with analgesics of the morphine type it enables the elimination of the injection treatment, which is very unconfortable and painful, for the first time. The said oral composition comprises preferably about 20–1000 parts by weight, particularly preferably 40 parts by weight of a homopyrimidazole compound for 1 part by weight of azidocodeine or the bitartarate thereof. A highly preferred embodiment of the present invention is a tablet or capsule comprising about 150–250 mg., particularly 200 mg. of 1,6-dimethyl-3-carbethoxy-4-oxo-6,7,8,9-tetrahydro-homopyrimidazolium-methosulphate and 2.5–10 mg., preferably 5 mg. of azidocodiene or the bitartarate thereof.

The parenteral compositions according to the present invention contain preferably 100–1000 parts by weight of a homopyrimidazole compound for each 1 part by weight of an azidocompound. A very preferred embodiment of the present invention is a parenteral composition (injectable solution, powder ampoule) comprising about 150–500 mg. of 1,6-dimethyl-3-carbethoxy-4-oxo-6,7,8,9-tetrahydro-homopyrimidazolium-methosulphate and about 0.2–0.5 mg. of azidomorphine-bitartarate.

The synergistic composition of the present invention may be prepared by methods of pharmaceutical industry known per se. The compositions for oral administration may be prepared by admixing the active ingredient with inert non-toxic carriers or diluents (e.g. cellulose, silicic acid, stearine, polyvinylpyrrolidone, talc, starch, etc.). The said composition may also contain the well known additives (e.g. emulsifying, suspending agents, dyes, salts for controlling the osmotic pressure, buffers, etc.).

The parenteral compositions of the present invention may be prepared in aqueous or non-aqueous medium. The non-aqueous preparations may be prepared in propylene glycol, polyethylene glycol or any other suitable solvents. Powder ampoules may be prepared preferably by introducing the homopyrimidazole derivative into a powder ampoule, dissolving an azidocompound in distilled water or in a suitable non-aqueous medium, in a solvent ampoule and dissolving a homopyrimidazole derivative of the powder ampoule before use in the content of the solvent ampoule.

The pharmaceutical compositions may also be finished in other suitable dosage unit forms according to known methods of pharmaceutical industry.

The synergistic analgesic activity of the combinations according to the present invention is shown and verified by the following comparative tests.

The preparation forming the object of our invention displays synergism regarding its analgesic effect. The activity of the combination significantly surpasses that of the individual components, consequently equianalgesic effect ($ED_{50}$) is obtained by much lower doses than that of the azidocompounds.

Synergism is measured with the help of the algolytic test (Knoll J.: Animal and Clinical Pharm. Techn. in Drug. Ev. [1967] 305–321). The test is suited only for the demonstration of the effect of major analgesics. The test compound is administered in various doses. Analgesia is evaluated by the following scale:

| Scores | |
|---|---|
| 20 | Violent |
| | Persistent vehement attempts to move: persistent crying |
| 15 | Intense |
| | Periodic attempts to move; persistent crying |
| 10 | Slight |
| | Occasional faint stirring, occasional crying on irritation |
| 5 | Very slight |
| | No stirring, occasional crying on strong irritation |
| 0 | None |
| | Remains still and keeps silent |

The results obtained are summarized in the following table:

TABLE A

| MZ - 144 | | | Azidocodeine | | | |
|---|---|---|---|---|---|---|
| Dose mg/kg | Mode of appl. | Pretr. time | Dose mg/kg | Mode of appl. | Pretr. time | Pain units |
| — | — | — | 30 | p.o. | 1 hour | 87 |
| — | — | — | 45 | p.o. | 1 hour | 38 |
| — | — | — | 60 | p.o. | 1 hour | 30 |
| 300 | p.o. | 1 hour | — | — | — | 75 |
| 300 | p.o. | 1 hour | 30 | p.o. | 1 hour | 57 |
| 300 | p.o. | 1 hour | 45 | p.o. | 1 hour | 0 |
| 300 | p.o. | 1 hour | 60 | p.o. | 1 hour | 0 |

It appears from the diagram plotted on the ground of the above data that $ED_{50}$ of azidocodeine in the algolytic test is 32 mg./kg., while that combination of azidocodeine and MA-144 is 12 mg./kg. p.o. (per oz) which unanimously proves the synergism between the two compounds.

MZ 144 means 1,6-dimethyl-3-carbethoxy-4-oxo-6,7,8,9-tetrahydro-homopyrimidazolium-methosulphate.

A further advantage of the synergistic preparation is the prolongation of the duration of the effect. A modified "hot plate test" was used in the experiments (Pórszász, J. and Herr, F.: Kisérl. Orvostud. ([1950] 2292). According to the results obtained in the test, the effect of azidocodeine lasts for 2–2.5 hours, while the duration of the effect of the combination azidocodeine + 1,6-dimethyl-3-carbethoxy-4-oxo-6,7,8,9-tetrahydro-homopyrimidazole-methosulphate is 3.5–4 hours.

Because of the synergism effect, the dose of the individual components of the preparation can be substantially reduced.

1. In order to show that Minor Analgesica (Algopyrin AP) does not considerably enhance the effect of stupefacient analgetics (such as azidomorphine AM and Azidocodeine AK), while homopyrimidazole derivatives have a strong synergic effect, we present the following data:

Table 1

Examination of PROBON'S potentiating effect upon azidomorphine and azidocodeine, carried out on rats, by hot plate test, compared with Algopyrine. The compounds were administered s.c. (subcutaneously).

| Minor Analgesics | | Azido derivatives | | Analgesic effect |
|---|---|---|---|---|
| Name | Dosage mg/kg | AM* mg/kg | AK* mg/kg | Hot plate test % |
| AP*** | 150 | — | — | 33 |
| | 200 | — | — | 49 |
| Probon | 50 | — | — | 38 |
| — | — | 0.015 | — | 22 |
| — | — | — | 0.250 | 16 |
| AP | 150 | 0.015 | — | 29 |
| | 150 | — | — | 29 |
| Probon | 50 | 0.015 | — | 79 |

Table 1-continued

Examination of PROBON'S potentiating effect upon azidomorphine and azidocodeine, carried out on rats, by hot plate test, compared with Algopyrine. The compounds were administered s.c. (subcutaneously).

| Minor Analgesics | | Azido derivatives | | Analgesic effect |
|---|---|---|---|---|
| Name | Dosage mg/kg | AM* mg/kg | AK* mg/kg | Hot plate test % |
| AM* azidomorphine | 50 | — | 0.250 | 68 |

AK = azidocodeine   AP* = Algopyrin

It can be seen from this survey that in a Hot plate test, the Algopyrin being equipotent with Probon, does not increase the analgesic effect of azidomorphine or of azido-codeine.

2. As to the question, as to what degree other homopyrimidazoles (besides Probon) increase the analgesic effect of the two azido derivatives, the next Table gives a detailed answer. Here we show the effect of a few homopyrimidazole derivatives which have similar effects as the Probon.

Table 2

Examination of the potentiating effect of a few homopyrimidazole derivatives upon axidomorphine or azidocodeine, carried out on rats, by Hot plate test, the compounds were administered s.c.

| Homopyrimidazole | | azido derivatives | | Analgesic effect |
|---|---|---|---|---|
| Name | Dosage mg/kg | AM mg/kg | AK mg/kg | Hot plate test % |
| — | — | 0.015 | — | 22 |
| — | — | — | 0.250 | 16 |
| MZ-108 | 200 | — | — | 18 |
| MZ-168 | 50 | — | — | 23 |
| MZ-170 | 300 | — | — | 31 |
| MZ-211 | 50 | — | — | 38 |
| MZ-108 | 200 | 0.015 | — | 59 |
| MZ-168 | 50 | 0.015 | — | 64 |
| MZ-170 | 300 | 0.015 | — | 53 |
| MZ-211 | 50 | 0.015 | — | 68 |
| MZ-108 | 200 | — | 0.250 | 48 |
| MZ-168 | 58 | — | 0.250 | 40 |
| MZ-170 | 300 | — | 0.250 | 48 |
| MZ-211 | 50 | — | 0.250 | 88 |

It can be seen from the test results that MZ-144 (see Table 1) combined with azidomorphine or azidocodeine shows a potentiating synergism.

The synergism found in the case of the homopyrimidazole derivatives given in Table 2 and of the azido derivatives is first of all of additive character.

About the potentiating effect of Probon and other homopyrimidazole derivatives (Phentanyl) we give the following information.

Table 3

Examination of the analgesic effect of a few homopyrimidazole derivatives combined with Phentanyl, carried out on rats, measured with algolytic test

| Homopyrimidazole derivatives | | | Phentanyl | | Analgesic effect algolytic test % |
|---|---|---|---|---|---|
| Name | mg/kg | way of adm. | mg/kg | way of adm. | |
| Probon | 250 | s.c. | — | — | 59 |
| MZ-108 | 300 | i.v. | — | — | 31 |
| MZ-211 | 50 | i.v. | — | — | 15 |
| — | — | — | 0.020 | i.v. | 27 |
| — | — | — | 0.040 | i.v. | 76 |
| Probon | 250 | s.c. | 0.020 | i.v. | 100 |
| | 250 | p.o. | 0.020 | i.v. | 50 |
| MZ-211 | 50 | i.v. | 0.030 | i.v. | 59 |
| MZ-108 | 300 | i.v. | 0.020 | i.v. | 49 |

In addition to the analgesic effect some narcosis potentiating test results are also given and the synergistic effect of the homopyrimidazole derivatives and butyrophenones is demonstrated.

Table 4

Examination of the narcosis potentiating effect of a few homopyrimidazole derivatives combined with butyrophenones carried out on rats, the compounds were administered i.v.

| Homopyrimidazole mg/kg | | Butyrophenone | | Prolongation of narcotic period % |
|---|---|---|---|---|
| | | phentanyl mg/kg | haloperidol | |
| MZ-144 | 25 | — | — | 571 |
| — | — | 0.025 | — | 667 |
| — | — | 0.010 | — | 129 |
| — | — | — | 0.5 | 255 |
| MZ-108 | 200 | 0.010 | — | 587 |
| -138 | 10 | 0.010 | — | 603 |
| -145 | 40 | 0.010 | — | 676 |
| -169 | 50 | 0.010 | — | 519 |
| -134 | 25 | 0.010 | — | 509 |
| -170 | 500 | 0.010 | — | 978 |
| MZ-144 | 25 | — | 0.5 | 1981 |
| -143 | 25 | — | 0.5 | 489 |
| -138 | 10 | — | 0.5 | 441 |
| -145 | 40 | — | 0.5 | 631 |
| -108 | 100 | — | 0.5 | 720 |
| -170 | 500 | — | 0.5 | 670 |

Remarks:
In the above tests the following compounds given with abbreviations have been used:
Probon (MZ-144): 1,6-dimethyl-3-carbethoxy-4-oxo-6,7,8,9-tetrahydro-homopyrimidazolium-methosulfate,
algopyrin: 2,3-dimethyl-4-methylamino-1-phenyl-5-pyrazolon-N-methane-sulfonic acid,
MZ-108: 3-carbethoxy-4-oxo-6-methyl-6,7,8,9-tetrahydro-homopyrimidazole,
MZ-168: 1,6-dimethyl-3-carbethoxy-4-oxo-1,6,7,8,9,10-hexahydro-homopyrimidazole,
MZ-170: 1,6-dimethyl-3-carbethoxy-4-oxo-1,2,3,6,7,8,9,10-octahydro-homopyrimidazole,
MZ-211: 1,6-dimethyl-4-oxo-6,7,8,9-tetrahydro-homopyrimidazole-3-carboxylic acid,
MZ-138: 1,6-dimethyl-3-carbethoxy-4-oxo-homopyrimidazolium-methosulfate,
MZ-145: 1,6-dimethyl-3-carbamoyl-4-oxo-6,7,8,9-tetrahydro-homopyrimidazolium-methosulfate,
MZ-169: 1-ethyl-6-methyl-3-carbethoxy-4-oxo-1,6,7,i,9,10-hexahydro-homopyrimidazole,
MZ-134: 6-methyl-3-carbethoxy-4-oxo-1,6,7,8,9,10-hexahydro-homopyrimidazole,
MZ-143: 1-ethyl-6-methyl-3-carbethoxy-4-oxo-6,7,8,9-tetrahydro-homopyrimidazolium-methosulfate
Phentanyl: 1-phenethyl-4-N-propionylanilino-piperidine.

In animal experiments it was found that the synergism in the analgesic effect of the compounds is not accompanied by addition of the side-effect, moreover the preparation referred to in the invention is practically devoid of side-effects. Thus, the combination containing azidocodeine and 1,6-dimethyl-3-carbethoxy-4-oxo-6,7,8,9-tetrahydro-homopyrimidazole-methosulphate in 1:40 proportion, according to clinical experience fails to depress respiration.

The analgesic affect was measured by the algolytic test developed and later modified by Knoll (Knoll, J.: Animal and Clinical Pharm. Techn. in Drug. Ev., 305–321). The method is a model of operational pain and as that is suited only for the demonstration of major analgesic effect. The test is based on the observation that 10 mg./kg. morphine administered i.v. to rats, produces more effective analgesia so that the animal endures laparatomy without pain response and muscular straining and does not show the slightest sign of prostration following the operation. Only complete relief of pain was taken as analgesic effect. Each dose was administered to a group of 10 rats and the animals displaying complete analgesia were expressed in percent of the controls. This was considered as the measure of analgesia.

The synergistic effect of the preparation forming the object of the present invention was determined on the basis of the combination containing azidomorphine and 1,6-dimethyl-3-carbethoxy-4-oxo-6,7,8,9-tetrahydro-homopyrimidazole-methylsulphate. The combination of per se ineffective doses of the components (0.062 mg./kg. azidomorphine + 100 mg./kg. s.c. homopyrimidazole derivative) produced a 80% effect, which means that the combination produced complete analgesia in 80% of the animals.

The advantageous synergism observed in the analgesic effect is not accompanied by the increase of toxicity.

Toxicity of combination was determined in Wistar rats of both sexes weighing 120–150 g. $LD_{50}$ values were calculated by the Litchfield-Wilcoxon method. Toxicity of a combination containing 75% of the $LD_{50}$ of two components was determined. The death rate in the population was 50%, i.e lower than expected, which means that synergism in the analgesic effect of the compounds is not accompanied by synergism in toxicity.

Further details of the present invention are to be found in the following Examples without limiting the scope of the invention to the Examples.

EXAMPLE 1

Tablets having the following compositions are prepared by admixing the components and pressing the mixture to tablet form.

| | |
|---|---|
| Azidocodeine | 5 mg. |
| 1,6-dimethyl-9-carbethoxy-4-oxo-6,7,8,9-tetrahydro-homopyramidazolium-methosulphate | 200 mg. |
| Titaniumdioxide | 3 mg. |
| Betaine hydrochloride | 3 mg. |
| Colloidal silicic acid | 13 mg. |
| Polyvinylpyrrolidone | 15 mg. |
| Stearine | 26 mg. |
| Crystalline cellulose | 76 mg |

EXAMPLE 2

500 mg. of 1,6-dimethyl-3-carbethoxy-4-oxo-6,7,8,9-tetrahydro-homopyrimidazolium-methosulphate are introduced in a powder ampoule. In a solvent ampoule 0.5 mg. of azidomorphine-bitartarate are dissolved in 5 ml. of distilled water. Before use the homopyrimidazolium-derivative of the powder ampoule is dissolved in the content of the solvent ampoule. The composition is suitable for intravenous administration. In use at surgical intervention the proposed dose is 1 ampoule.

EXAMPLE 3

A parenteral preparation having the following composition is prepared:

| | |
|---|---|
| 1,6-dimethyl-3-carbethoxy-4-oxo-6,7,8,9-tetrahydro-homopyrimidazolium-methosulphate | 200 mg. |
| Azidomorphine-bitartarate | 0.2 mg. |
| Distilled water q.s. | 2. ml |

The injectable solution thus obtained is filled into ampoules.

EXAMPLE 4

A known aqueous parenteral composition is prepared having the following composition:

| | |
|---|---|
| 1,6-dimethyl-3-carbethoxy-4-oxo-6,7,8,9-tetrahydro-homopyrimidazolium-methosulphate | 150 mg. |
| Azidomorphine-bitartarate | 0.5 mg. |
| Propylene glycol | 0.66 ml. |
| Polyethylene glycol | 0.66 ml. |
| Cellosolve | 0.66 ml. |

The injectable solution thus obtained is filled into ampoules. The solution is very stable; during storage at 20° C for 5 years the decomposition is but a few percent.

We claim:
1. A pharmaceutical composition of synergistic analgesic activity comprising one part of an azidocompound of the formula

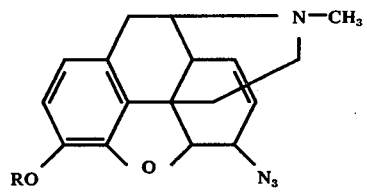

or a salt thereof, wherein R is hydrogen, methyl, ethyl or acetyl and 20 to 1000 parts of a pyrimidazolium compound of the formula

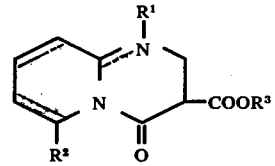

wherein $R^1$, $R^2$ and $R^3$ are hydrogen or lower alkyl with 1 to 6 carbon atoms and the dotted lines represent optionally hydrogenated bonds, or a pharmaceutically acceptable sale or quaternary salt thereof in admixture with a suitable inert solid or liquid carrier or diluent.

2. Pharmaceutical compositions according to claim 1, wherein the azido compound is azidomorphine, azidocodeine or a salt, preferably the bitartarate thereof.

3. Pharmaceutical compositions according to claim 1 wherein the pyrimidazolium compound is 1,6-dimethyl-3-carbethoxy-4-oxo-6,7,8,9-tetrahydro-homopyrimidazolium-methosulphate.

4. A pharmaceutical analgesic composition, comprising as the effective constituents 20 to 1000 parts by weight of 1,6-dimethyl-3-carbethoxy-4-oxo-6,7,8,9-tetrahydro-homopyrimidazolium-methosulphate per 1 part by weight of azidocodeine or a salt thereof.

5. A pharmaceutical composition according to claim 4, comprising in orally administrable dosage units about 150 to 250 mg. of 1,6-dimethyl-3-carbethoxy-4-oxo-6,7,8,9-tetrahydro-homopyrimidazolium-methosulphate and about 2.5 to 10 mg. of azidocodeine or the bitartarate thereof.

6. A pharmaceutical composition according to claim 1, comprising about 100 to 1000 parts by weight of 1,6-dimethyl-3-carbethoxy-4-oxo-6,7,8,9-tetrahydrohomopyrimidazolium-methosulphate per 1 part by weight of azidomorphine or a salt thereof.

7. A pharmaceutical analgesic parentenally administrable composition comprising about 150 to 500 mg. of 1,6-dimethyl-3-carbethoxy-4-oxo-6,7,8,9-tetrahydrohomopyrimidazolium-methosulphate and about 0.2–0.5 mg. of azidomorphine or the bitartarate thereof.

8. In an analgesic composition, the synergistic combination of 300 parts by weight of 1,6-dimethyl-3-carbethoxy-4-oxo-6,7,8,9-tetrahydro-homopyrimidazolium-methosulphate with substantially 45 to 60 parts by weight of azidomorphine or azidocodeine bitartarate.

* * * * *